United States Patent [19]

Hörenz

[11] Patent Number: 4,614,411
[45] Date of Patent: Sep. 30, 1986

[54] MICROSCOPE WITH CORRELATABLE FIXATION TARGET

[75] Inventor: Peter G. Hörenz, Hartsdale, N.Y.

[73] Assignee: Carl-Zeiss-Stiftung, Heidenheim/Brenz, Oberkochen, Fed. Rep. of Germany

[21] Appl. No.: 734,616

[22] Filed: May 16, 1985

[51] Int. Cl.$^4$ .................... A61B 3/10; G02B 21/06; G02B 21/22
[52] U.S. Cl. .................... 350/516; 350/526; 350/527; 351/211; 351/221
[58] Field of Search .............. 350/516, 515, 523, 527, 350/526, 514; 351/221, 211, 217, 218, 205, 210

[56] References Cited

U.S. PATENT DOCUMENTS

| | | | |
|---|---|---|---|
| 3,879,113 | 4/1975 | Howland et al. | 351/221 |
| 3,909,106 | 9/1975 | Buhter | 350/526 |
| 4,196,979 | 4/1980 | Kohayakawa et al. | 351/208 |
| 4,279,478 | 7/1981 | Matsumura | 351/221 |
| 4,436,388 | 3/1984 | Takahashi et al. | 351/208 |
| 4,443,079 | 4/1984 | Crane | 351/221 |
| 4,477,159 | 10/1984 | Mizuno et al. | 351/205 |
| 4,478,499 | 10/1984 | Hoerenz | 351/221 |

FOREIGN PATENT DOCUMENTS 111508 7/1982 Japan .................... 350/523

Primary Examiner—Jon W. Henry
Attorney, Agent, or Firm—Hopgood, Calimafde, Kalil, Blaustein & Judlowe

[57] ABSTRACT

The invention contemplates a binocular ophthalmological operation microscope with an optical fixation mark defined as effectively a point source of light, at the output end of an optical-fiber cable, wherein the output end faces the patient on the mechanically central axis of the microscope, i.e., on an alignment centered between and in the geometric plane defined by the respective binocular-viewing axes. The illumination system for the optical-fiber cable has provision for selective adjustment of the brightness of light output from the cable, thereby permitting selection of a brightness level which is comfortable to the patient and which also enables the observing physician to see the optical-fiber output as a cornea-reflected light spot, within his field of view. The spot size is small compared to the diameter of the observed pupil, so that the physician can know (from reflected-spot position, in relation to observed pupil position) when the patient's viewing axis and the physician's view of the reflected spot are exactly correlated.

6 Claims, 1 Drawing Figure

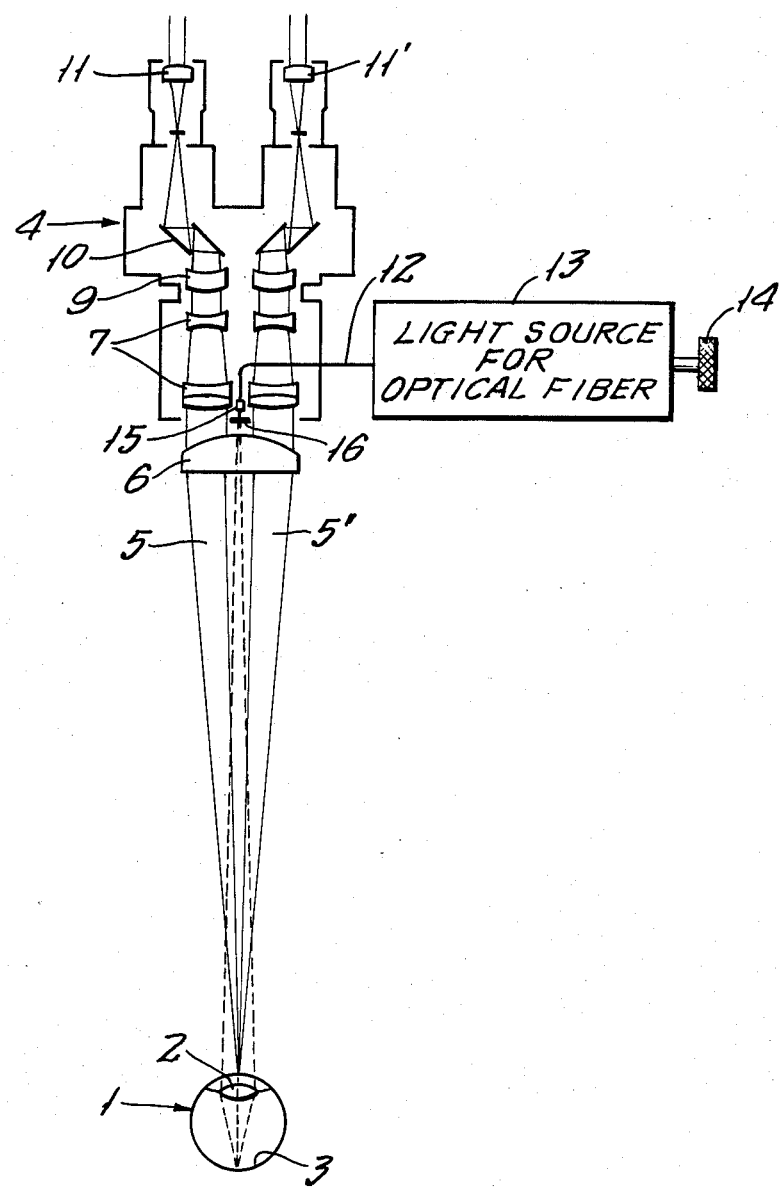

MICROSCOPE WITH CORRELATABLE FIXATION TARGET

BACKGROUND OF THE INVENTION

The present invention relates to an operation microscope, particularly for ophthalmological microsurgery.

It is necessary in certain procedures of ophthalmological surgery for the patient to bring the visual axis of his eye as closely as possible into the direction of observation (instrument central axis) of the operation microscope and to hold it there for a relatively long time. My U.S. Pat. No. 4,478,799 discloses several alternatives for meeting this need, with fixation-target projection through the single main objective of a binocular microscope.

In certain other ophthalmological procedures, it is desired to mark the optical zone of the cornea whereby it can be known that subsequent operative manipulations can be accurately referenced to the optical zone. Such marking may illustratively take the form of using a ring tool to temporarily impress an indented circular "mark" on the anterior surface of the cornea. The fixation devices of my said patent are unequal to this task, for binocular viewing, largely because there is no means whereby the physician can know that his indenting tool is centered on the visual axis of the eye under observation.

BRIEF STATEMENT OF THE INVENTION

It is an object of the invention to provide an improved binocular microscope and fixation device of the character indicated whereby the physician can also use the fixation device and can know when the patient's viewing-axis alignment with the fixation device is correlated with the physician's view of the fixation device, in the context of the observed field of view.

The invention achieves this object by so positioning the output end of an optical-fiber cable as to face the patient on the mechanically central axis of the microscope, i.e., on an alignment centered between the respective binocular-viewing axes. The illumination system for the optical-fiber cable has provision for selective adjustment of the brightness of light output from the cable, thereby permitting selection of a level of brightness which is comfortable to the patient and which enables the observing physician to see the optical-fiber output as a cornea-reflected light spot within his field of view. The spot is of size which is small compared to the diameter of the observed pupil, so that the physician can know (from reflected-spot position, in relation to observed pupil position) when the patient's viewing axis and the physician's view of the reflected spot are exactly correlated.

DETAILED DESCRIPTION

The invention will be described for a preferred embodiment in conjunction with the accompanying single drawing, which is an optical diagram of a binocular stereo operation microscope incorporating the fixation-mark feature of the invention.

In the drawing, 1 designates the eye of the patient, 2, the lens of the eye, and 3 the retina. A binocular microscope 4 has two observation-ray paths 5—5', the axis of each of which is in the plane of the drawing. A single main objective 6 enables focus of both observation-ray paths upon the anterior surface of eye 1, i.e., on the cornea; and the central axis of objective 6 is also in the plane of the drawing, being central between the axes of paths 5—5'. Each viewing system is shown to include a magnification changer 7 and an ocular system 9-10-11.

A fixation device of the invention comprises an optical-fiber cable 12 and an illumination system 13 with selectively adjustable means such as a knob 14 for adjusting the brightness level of light transmitted via cable 12 to the output end of the cable. This output end constitutes the fixation mark which serves the purposes of the invention. The output end is suitably a flat truncated face of a single suitably clad optical fiber and is fixedly held by a mount 15 so as to face the patient. The flat face is normal to the fiber axis which, at mount 15, is aligned with the central axis of the microscope, i.e., in the plane of the drawing and centered between axes of the viewing-ray paths 5—5'. Preferably, the effective diameter of the fixation mark (i.e., output face of the fiber of cable 12) is 1 millimeter or less, and as shown, the mount 15 is immediately behind the objective 6.

It is generally preferred that light from cable 12 shall be the only source of illumination of the object, namely, the eye of the patient. The intensity of cable-output luminance must in that case be sufficient (on the patient's eye) for the observing physician to see the patient's eye through the microscope and to perceive enough detail for performance of safe manipulations.

The small size of the output end of cable 12 provides the patient with a fixation target or fixation mark which is effectively a point light source. When the optical axis of the eye 1 is directed toward this fixation mark, the eye axis will be coaxially aligned with the mechanically central axis of the microscope, thus creating absolute symmetry (correlation) between the axis of observer viewing and the axis of patient viewing. The observing physician can know when this absolute condition is reached because he sees the corneal reflection of the point light source, in relation to the illuminated field, e.g., in relation to and within his view of the pupil of eye 1.

The fixation target will, because of its sufficient luminance, be bright enough for the creation of a virtual image by the cornea of the patient. This image is created 2 mm to 5 mm below the anterior surface of the cornea and thus can be viewed with medium-range magnification, so that both the cornea and the fixation target are simultaneously focused, allowing manipulations (on the eye) which are directly correlated both to the viewing axis of the patient and to the virtual image of the fixation target. Such a manipulation may illustratively include use of an annular ring tool to locally indent the anterior surface of the cornea, to thus transiently "mark" the optical zone, as a reference for the surgical execution of radial keratotomy incisions.

The ratio of brightness of the illuminated eye of the patient versus brightness of virtual image is estimated to be in the order of 1:50, but in any event is adjustable by manipulation of knob 14 to establish optimal viewing conditions for both the physician and his patient.

While it is possible that the described physician/patient correlation can be achieved for most patients (including many myopic patients) with the structure that has been described, it will be understood that the described structure lends itself to further optimalization for the particular patient by provision of an indexible carrier, for a succession of spaced corrective optical elements, selectively positionable on the central axis, as on an indexible transverse slide (suggested at 16) interposed between the optical-cable mount 15 and objective 6. Such a slide 16 will be understood to extend and to be indexibly positionable along a path normal to the plane of the drawing and to include plural corrective elements in the manner discussed for an indexible turret in my said patent. In this way, any patient can be given the comfort of a clearly focused fixation target.

Although the invention has been described in detail for a preferred embodiment, it will be understood that modifications and further detail may be developed without departure from the claimed scope of the invention. Thus, the optical-fiber cable 12 may be based on a single optical fiber or a bundle of optical fibers having a collective effective diameter in the indicated size range. Also, the output face of optical-fiber transmission may be optically finished other than to a flat, as for purposes of optimal object-field illumination.

Still further, it will be appreciated that, although desirable, it is not necessary for the point source of light at 15 to be the only source of object-field illumination. For example, the microscope 4 or the operating room may have other sources of light which wholly or partly illuminate the object field of view, and such other sources may be a cause of distracting the patient. But the fact remains that, with the invention, the observing physican can always know (by his watch of the corneal reflection of the point source in relation to the illuminated cornea and pupil) when his patient has correctly aligned his eye with the fixation target.

What is claimed is:

1. In a binocular operation microscope wherein a single main objectiveserves each of two spaced optical systems for an observing physician and has the capability of focusing said optical systems at the anterior surface of the eye of a patient under observation, and wherein a fixation-mark and light-projection system therefor also utilizes said main objective in its optical path of fixation-mark projection, the improvement wherein the fixation mark is the output end of an optical-fiber cable located behind and facing said objective lens and on the central axis of the microscope and between said optical systems, and wherein the light-projection system includes a light source with input to the other end of said optical-fiber cable and with means for selectively varying the intensity of light input to said optical-fiber cable, whereby an intensity level may be adjusted at which the physician can see a cornea-reflected image of the fixation mark in the context of the pupil of the observed eye and can be certain when the patient has aligned the observed eye upon the fixation mark, thus allowing manipulations on the eye which manipulations are directly correlated both to the viewing axis of the patient and the virtual image of the fixation target.

2. The binocular operation microscope of claim 1, in which the intensity of light input to said optical-fiber cable is continuously variable over a range which includes the ratio of approximately 1:50 for brightness illumination of the eye versus brightness of the virtual image created by the cornea of the eye under observation.

3. The binocular operation microscope of claim 1, wherein the effective diameter of the output end of said optical-fiber cable is in the order of 1 millimeter or less.

4. The binocular operation microscope of claim 1, wherein an indexibly positionable carrier of spaced plural corrective lens elements is so interposed between said output end and said objective as to enable indexing of a selected corrective element into the central axis of fixation-mark viewing.

5. In a binocular operation microscope having two spaced viewing optical systems adapted for concurrent focus at the anterior surface of the eye of a patient under observation, and wherein a fixation-mark and light-projection system projects the fixation mark on an axis at close offset from the axis of at least one of said viewing optical systems, the improvement wherein the fixation mark is the output end of an optical-fiber cable located on the central axis of the microscope and centrally between said viewing optical systems, and wherein the light-projection system includes a light source with input to the other end of said optical-fiber cable and with means for selectively varying the intensity of light input to said optical-fiber cable, whereby an intensity level may be adjusted at which the physician can see a cornea-reflected image of the fixation mark in the context of the pupil of the observed eye and can be certain when the patient has aligned the observed eye upon the fixation mark, thus allowing manipulations on the eye which manipulations are directly correlated both to the viewing axis of the patient and the virtual image of the fixation target.

6. The binocular operation microscope of claim 5, wherein an indexibly positionable carrier of spaced plural corrective lens elements is so interposed between said viewing optical systems as to enable indexing of a selected corrective element into the central axis of fixation-mark viewing.

* * * * *